United States Patent
Hotha

(10) Patent No.: US 9,018,225 B1
(45) Date of Patent: Apr. 28, 2015

(54) RIFAXIMIN CRYSTALLINE FORMS AND METHODS OF PREPARATION THEREOF

(71) Applicant: Kishore Kumar Hotha, Somerset, NJ (US)

(72) Inventor: Kishore Kumar Hotha, Somerset, NJ (US)

(73) Assignee: Novel Laboratories, Somerset, NJ (US)

( * ) Notice: Subject to any disclaimer, the term of this patent is extended or adjusted under 35 U.S.C. 154(b) by 0 days.

(21) Appl. No.: 14/338,447

(22) Filed: Jul. 23, 2014

Related U.S. Application Data

(60) Provisional application No. 61/858,884, filed on Jul. 26, 2013.

(51) Int. Cl.
*A61K 31/437* (2006.01)
*C07D 498/22* (2006.01)

(52) U.S. Cl.
CPC ............ *C07D 498/22* (2013.01); *A61K 31/437* (2013.01)

(58) Field of Classification Search
USPC .......................................... 514/279; 540/455
See application file for complete search history.

(56) References Cited

U.S. PATENT DOCUMENTS

| | | | |
|---|---|---|---|
| 4,341,785 A | 7/1982 | Marchi et al. | |
| 4,557,866 A | 12/1985 | Cannata et al. | |
| 7,045,620 B2 | 5/2006 | Viscomi et al. | |
| 7,612,199 B2 | 11/2009 | Viscomi et al. | |
| 7,902,206 B2 | 3/2011 | Viscomi et al. | |
| 7,906,542 B2 | 3/2011 | Viscomi et al. | |
| 7,915,275 B2 | 3/2011 | Viscomi et al. | |
| 7,923,553 B2 | 4/2011 | Viscomi et al. | |
| 7,928,115 B2 | 4/2011 | Forbes et al. | |
| 8,158,644 B2 | 4/2012 | Viscomi et al. | |
| 8,158,781 B2 | 4/2012 | Viscomi et al. | |
| 8,193,196 B2 | 6/2012 | Viscomi et al. | |
| 2005/0272754 A1* | 12/2005 | Viscomi et al. ............... | 514/279 |

OTHER PUBLICATIONS

Viscomi, G. C., et al., "Crystal forms of rifaximin and their effect on pharmaceutical properties", Cryst Eng Comm, 2008, 10, 1074-1081, (May 28, 2008), 1074-1081.

* cited by examiner

*Primary Examiner* — Charanjit Aulakh
(74) *Attorney, Agent, or Firm* — Schwegman Lundberg & Woessner, P.A.

(57) ABSTRACT

The present invention is directed to methods for preparation of a composition comprising mixed crystalline polymorphs rifaximin α and rifaximin β. For example, practice of a method of the invention can provide the composition comprising mixed crystalline polymorphs rifaximin α and rifaximin β wherein the rifaximin β is present in about 3-12% (w/w) or is present in about 5-8% (w/w). The composition comprising mixed crystalline polymorphs rifaximin α and rifaximin β is prepared by dissolving raw rifaximin in a water-soluble organic solvent, for example ethanol, at reflux, then adding water to achieve a final mixed solvent of about 7:3 (v/v) solvent to water ratio, then cooling to 35-40° C. until crystallization commences, then further cooling with stirring to 0° C., then recovery of the crystallized material, and drying to a water content of between 2.5% and 5.0%, to provide the composition comprising mixed crystalline polymorphs rifaximin α and rifaximin β. The composition is suitable for medicinal use, such as in treatment of infections of the gastrointestinal tract.

12 Claims, No Drawings

RIFAXIMIN CRYSTALLINE FORMS AND METHODS OF PREPARATION THEREOF

CLAIM OF PRIORITY

This application claims the benefit of priority of U.S. Provisional Patent Application Ser. No. 61/858,884, entitled "RIFAXIMIN CRYSTALLINE FORMS AND METHODS OF PREPARATION THEREOF," filed on Jul. 26, 2013, the benefit of priority of which is claimed hereby, and which is incorporated by reference herein in its entirety.

BACKGROUND

Rifaximin is a semi-synthetic, non-systemic antibiotic that can be derived from rifamycin O by condensation with 2-amino-4-methylpyridine. Xifaxan® has Rifaximin as the active ingredient, and its labels are hereby incorporated by reference.

The U.S. Pat. No. 4,341,785, U.S. Pat. No. 4,557,866, U.S. Pat. No. 7,045,620, U.S. Pat. No. 7,612,199, U.S. Pat. No. 7,902,206, U.S. Pat. No. 7,906,542, U.S. Pat. No. 7,928,115, U.S. Pat. No. 7,915,275, U.S. Pat. No. 7,923,553, U.S. Pat. No. 8,158,644, U.S. Pat. No. 8,158,781, and U.S. Pat. No. 8,193,196 provide methods for the synthesis of polymorphic forms of rifaximin and are hereby incorporated by reference in their entireties.

The U.S. Pat. No. 4,341,785 describes the preparation and use of new imidazo-rifamycin derivatives of a general formula which includes the antibiotic rifaximin, having the structure

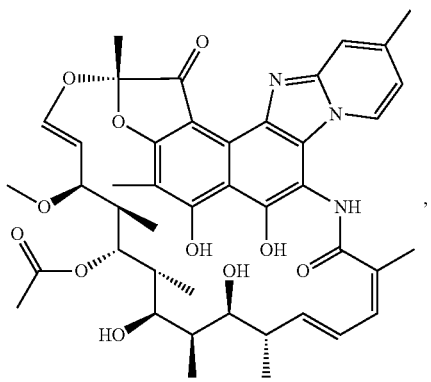

among the compounds claimed therein.

In U.S. Pat. No. 4,557,866, a process is described for conversion of rifamycin O to rifaximin by contacting rifamycin O with 2-amino-4-methylpyridine. The product was purified by crystallization from ethanol/water 7:3.

The U.S. Pat. No. 7,045,620 describes crystalline polymorphous forms of rifaximin, named rifaximin α and rifaximin β, and a poorly crystalline form named rifaximin γ. These forms were described as obtained by means of a crystallization process carried out by hot-dissolving the raw rifaximin in ethyl alcohol and by causing the crystallization of the product by the addition of water at a determinate temperature and for a determinate period of time. The crystallization was followed by drying carried out under controlled conditions until a specific water content was reached in the end product. The rifaximin α and rifaximin β crystalline polymorphs were characterized by X-ray diffractogram properties. It is described that the production of rifaximin α and rifaximin β during drying depends on the amount of water remaining at the end, higher or lower than 4.5%, and not from the experimental conditions of pressure and temperature at which this critical limit of water percentage is achieved. In fact, the two polymorphous forms, with higher or lower water content, can be obtained by drying under vacuum or at atmospheric pressure, at room temperature or at high temperatures, in the presence or in the absence of drying agents, provided that the drying is conducted for the amount of time necessary so that the water percent characteristic for each polymorphous form is achieved. It is described in the U.S. Pat. No. 7,045,620 that polymorphous form rifaximin β is obtained when the drying of the product, crystallized and washed with water, is stopped at values of water higher than 4.5% and that the polymorphous form rifaximin α is obtained by continuing the drying until values lower than 4.5%, preferably between 2.0% and 3.0%, are reached. The polymorphous form rifaximin α, kept in an ambient environment with a relative humidity higher than 50% for a period of time between 12 and 48 hours, turns into the polymorphous form β, which in turn, by drying until an amount of water lower than 4.5% is reached, preferably comprised between 2.0% and 3.0%, turns back into the polymorphous form rifaximin α.

In U.S. Pat. No. 7,612,199, it is disclosed that the polymorph called rifaximin α is characterized by a water content lower than 4.5%, preferably between 2.0% and 3.0% and from a powder X-ray diffractogram which shows peaks at the values of the diffraction angles 2θ of 6.6°; 7.4°; 7.9°; 8.8°; 10.5°; 11.1°; 11.8°; 12.9°; 17.6°; 18.5°; 19.7°; 21.0°; 21.4°; 22.1°. The polymorph called rifaximin β is characterized by a water content higher than 4.5%, preferably between 5.0% and 6.0%, and by a powder X-ray diffractogram which shows peaks at the values of the diffraction angles 2θ of 5.4°; 6.4°; 7.0°; 7.8°; 9.0°; 10.4°; 13.1°; 14.4°; 17.1°; 17.90; 18.30; 20.9° The polymorph called rifaximin γ is characterized by a powder X-ray diffractogram much poorer because of the poor crystallinity; the significant peaks are at the values of the diffraction angles 2θ of 5.0°; 7.1°; and 8.4°.

Crystal forms of rifaximin and their effect on pharmaceutical properties, are further described in Viscomi G C, et al, *The Royal Society of Chemistry, CrystEngComm,* 2008, 10, 1074-1081, which is hereby incorporated by reference in its entirety.

U.S. Pat. No. 8,158,781 and U.S. Pat. No. 8,158,644 claim the individual α, β, and γ crystalline polymorphs of rifaximin.

SUMMARY

The present invention is directed, in various embodiments, to methods for the manufacture of mixed crystalline polymorphs rifaximin α and rifaximin β.

In various embodiments, the invention can provide a method for the manufacture of a composition comprising mixed crystalline polymorphs rifaximin α and rifaximin β, comprising (a) dissolving rifaximin in a water-soluble organic solvent and warming the organic solvent to reflux; then, when the rifaximin is completely dissolved in the organic solvent to provide a solution of rifaximin in the organic solvent, (b) adding water to the solution to provide a second solution of rifaximin in a mixed solvent, the mixed solvent having an organic solvent to water ratio of about 5:5 to about 9:1 (v/v), to provide the second solution of rifaximin in the mixed solvent; then, (c) cooling the second solution to a temperature of 25-50° C., and stirring at the temperature of 25-50° C. until crystallization takes place, then (d) cooling the solution to about 0° C. with stirring, then, (e) recovering the crystallized material, then (f) drying the crystallized material to a water content of between 2.5% and 5.0%;

to provide the composition comprising mixed crystalline polymorphs rifaximin α and rifaximin β.

In various embodiments, the composition can be a mixture of a majority percentage of the α refaximin polymorph and a minority percentage of the β refaximin polymorph, preferably about 3% up to and including about 45% of the β refaximin polymorph with the remainder being the α refaximin polymorph, more preferably about 3% up to and including about 30% of the β refaximin polymorph with the remainder being the α refaximin polymorph; especially more preferably about 3% up to and including about 20% of the β refaximin polymorph with the remainder being the α refaximin polymorph; most preferably about 3-12% of the β polymorph mixed with a remainder of the α rifaximin polymorph; or especially most preferably the composition can be a mixture of about 5-8% of the β polymorph mixed with a remainder of the α rifaximin polymorph.

By practicing a method of the invention as disclosed and claimed herein, a composition comprising mixed crystalline polymorphs of rifaximin can be obtained rather than only a single crystalline polymorph. The composition can be suitable for use in the formulation of medicaments, such as for the treatment of infections of the gastrointestinal (GI) tract.

A pharmaceutical composition useful as such a medicament can be formulated by combination of the Rifaximin mixed α and β polymorphs and a suitable pharmaceutical carrier. The percentage of α and β polymorph of the mixture can be any percentage given above. The pharmaceutical carrier includes those suitable for oral administration and preferably ready dissolution in the GI tract.

Xifaxan® has Rifaximin as the active ingredient, and its labels are hereby incorporated by reference.

DETAILED DESCRIPTION

A crystal polymorph or crystalline polymorph, as the term is used herein, refers to each one of a plurality of crystalline forms that an organic compound can assume in the solid state. As is well known in the art, the crystal form, i.e., as defined by the space group of the crystal, is determined by the configuration of individual molecules of the compound that form the unit cell of the crystal. Often, solid substances will crystallize in one of several forms, and these various forms are termed crystal polymorphs or crystalline polymorphs of the substance. The form a crystal of a compound will take upon crystallization has been found in the art to be highly dependent upon the conditions of crystallization, including solvent(s), temperature, time, agitation (stirring), rate of cooling, time of cooling, seeding, and the like.

A compound, when solid, can be composed of crystals of only one of several possible polymorphs, or can be composed of mixtures of crystals of different polymorphic forms. While typically each individual crystal is a single crystalline polymorphic form, it is also possible for solid forms of compounds to contain crystals or quasi-crystals composed of crystalline domains of more than a single polymorphic form. Alternatively, a sample that contains mixed polymorphic forms can contain individual crystals each of a defined single polymorphic form, but the macroscopic sample comprising crystals of more than a single polymorphic form.

It is also well-known in the art that different crystalline polymorphs of an organic compound can display differing physical properties, such as rate of dissolution, which can be important in the formulation of the compound for use as a medicinal substance (medicament). Different crystalline polymorphs can thus have differing release profiles when the medicament is administered as a solid, and dissolution occurs in the gastrointestinal GI tract.

Rifaximin is used as a non-systemic antibiotic, as it is absorbed little or not at all through the wall of the stomach or intestine when administered orally. As there is little or no uptake into the blood stream when the antibiotic rifaximin is administered orally, for non-GI infections is must be administered parenterally, and thus the most prevalent use for rifaximin is in the treatment of GI conditions where blood absorption is not required.

In the treatment of GI infections and the like, the rate of dissolution of the solid rifaximin in the liquids of the GI tract is a significant factor in determining the site and rate of passage of the antibiotic into solution, which is needed prior to any uptake by bacteria or the like. The bacteria must absorb the antibiotic for the antibiotic to have its lethal effect on the infective organisms.

The present invention is directed to methods for preparation of solid samples of rifaximin wherein a mixture of crystalline polymorphs is present in the solid sample of rifaximin. In various embodiments, the invention provides methods for conversion of "raw" or "residue" rifaximin, i.e., the molecular species as recovered from its preparation (e.g., from rifamycin O and 2-amino-4-methylpyridine), into a solid sample comprising a mixture of the rifaximin α and rifaximin β crystalline polymorphic forms.

Accordingly, in various embodiments, the invention can provide a method for the manufacture of a composition comprising mixed crystalline polymorphs rifaximin α and rifaximin β, comprising (a) dissolving rifaximin in a water-soluble organic solvent and warming the organic solvent to reflux; then, when the rifaximin is completely dissolved in the organic solvent to provide a solution of rifaximin in the organic solvent, (b) adding water to the solution to provide a second solution of rifaximin in a mixed solvent, the mixed solvent having an organic solvent to water ratio of about 5:5 to about 9:1 (v/v), to provide the second solution of rifaximin in the mixed solvent; then, (c) cooling the second solution to a temperature of 25-50° C., and stirring at the temperature of 25-50° C. until crystallization takes place, then (d) cooling the solution to about 0° C. with stirring, then, (e) recovering the crystallized material, then (f) drying the crystallized material to a water content of between 2.5% and 5.0%;

to provide the composition comprising mixed crystalline polymorphs rifaximin α and rifaximin β.

For example, the organic solvent to water ratio can be about 7:3 (v/v).

For example, the cooling of the second solution can be to a temperature of 35-40° C., and stirring at the temperature of 35-40° C. continued until crystallization takes place.

The term "water-soluble organic solvent" as used herein refers to a solvent that is soluble in water when in a mixed solvent having about 70% (by volume) of the organic solvent and about 30% (by volume) water. For example, the water-soluble organic solvent can be an alcohol, such as ethanol, or such as methanol, isopropanol, n-propanol, methoxyethanol, ethoxyethanol, and the like. Or, the water-soluble organic solvent can be a ketone, such as acetone. or the water-soluble organic solvent can be a water-soluble ether, such a dimethoxyethanol. Or, the water-soluble organic solvent can be a mixture, such as a mixture of different alcohols, or a mixture of alcohols and ketones, or alcohols and ethers, or all together, and the like, provided that the organic solvent and water are mutually soluble at a ratio of about 7:3 (v/v) solvent to water (v/v).

The composition comprising mixed crystalline polymorphs rifaximin α and rifaximin β can comprise various ratios of the two polymorphic crystalline forms rifaximin α and rifaximin β. For example, the composition obtained by practice of a method of the invention can comprise mixed crystalline polymorphs rifaximin α and rifaximin β wherein a majority percentage of the mixture is the α polymorph with a minority percentage being the β polymorph. Preferably the mixture can be about 3% up to 45% β polymorph with the remaining percentage being the α polymorph. More preferably, the mixture can be about 3% up to about 30% β with the remaining percentage of the mixture being α. Especially more preferably, the mixture can be about 3% up to about 20% β with the remaining percentage being α. Most preferably, the mixture can be about 3-12% (w/w) of the rifaximin β crystalline polymorph in mixture with the remaining percentage of the rifaximin α crystalline polymorph. Especially most preferably, the composition comprising mixed crystalline polymorphs rifaximin α and rifaximin β can contain about 5-8% (w/w) of the rifaximin β crystalline polymorph in the mixture with the rifaximin α crystalline polymorph, in the solid composition that is obtained by practice of an embodiment of the method disclosed and claimed herein.

In various embodiments of the inventive method, a sample of rifaximin, e.g., of purity suitable for use in administration to a patient in need thereof or in formulation of a medicament for administration to a patient in need thereof, is dissolved in the water-soluble organic solvent. This starting sample of rifaximin can be obtained by the semi-synthetic conversion of, e.g., rifamycin O, obtainable from natural (fermentation) sources, to rifaximin by reaction with 2-amino-4-methylpyridine (2-amino-γ-picoline), under conditions optionally further comprising iodine, as outlined in the synthetic procedures provided in the Examples, below.

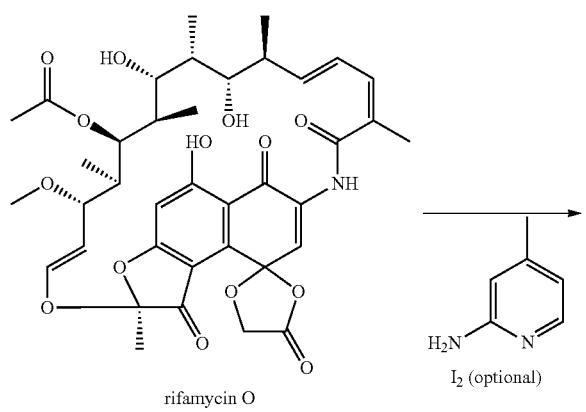

rifamycin O

I₂ (optional)

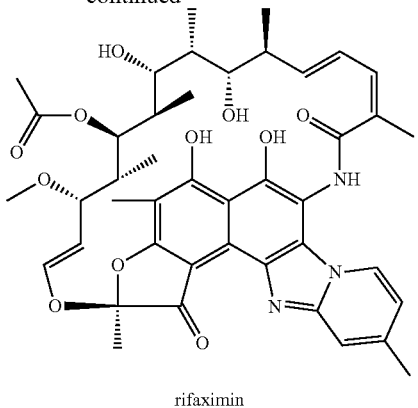

rifaximin

Any sample of rifaximin of suitable chemical purity for pharmaceutical use can be employed. The first step of the inventive method is:

(a) dissolving rifaximin in a water-soluble organic solvent and warming the organic solvent to reflux and when the rifaximin is completely dissolved in the organic solvent to provide a solution of rifaximin in the organic solvent.

The refluxing and dissolving of the rifaximin can be carried out in any method known to the person of skill in the art, i.e., in a round-bottom flask or a large-scale reactor, fitted with a reflux condenser, stirring means, and means for subsequent addition of water to the hot, refluxing solution of rifaximin. Typically, on a larger scale, stirring is accomplished by means of an overhead stirrer fitted with a paddle and shaft of non-reactive materials, i.e. Teflon or stainless steel paddle and glass or metal shaft. The reflux condenser can be of any suitable construction. The dissolution step can be carried out under inert gas, e.g., nitrogen or argon atmosphere, or can be carried out under ambient atmospheric conditions.

As noted above, the solvent can be an alcohol, such as ethanol, methanol, isopropanol, n-propanol, methoxyethanol, ethoxyethanol, or the like, or can be a ketone such as acetone, or can be a water-soluble ether such as dimethoxyethanol, etc.

The determination that dissolution of the rifaximin has taken place, i.e., that solution is complete, can be made visually, e.g., using a sight tube on a reactor, or simply viewing the contents of a glass flask, or can be made using standard optical equipment to measure % transmittance or the like. Complete solution of the rifaximin is needed prior to addition of water in the second step. If insoluble materials other than rifaximin are present, it is possible to remove them by filtration prior to addition of the water.

In the second step, the clear solution of rifaximin in the organic solvent is kept at the temperature at or near reflux, then:

(b) adding water to the solution to provide a second solution of rifaximin in a mixed solvent, the mixed solvent having an organic solvent to water ratio of about 7:3 (v/v), to provide the second solution of rifaximin in the mixed solvent.

This step can be carried out in the same flask or reactor that was used to dissolve the rifaximin in the water-soluble organic solvent. Water can be added over a period of time, such as about 30 minutes, while maintaining the warm temperature at or near the reflux point of the organic solvent. Any suitable apparatus, such as an addition funnel or tube, can be used that is compatible with the vessel and the reflux condenser setup. Water can be added dropwise with stirring, to avoid local high concentrations of water that could results in premature precipitation of solid rifaximin, prior to the desired step of crystallization. Water addition is continued until a volume to volume (v/v) ratio of about 7 parts organic solvent and about 3 parts water is achieved, providing the second solution comprising rifaximin in the aqueous organic solvent mixture.

After the target ratio of organic solvent and water is reached, the solution should still be complete at the elevated temperature, i.e., premature precipitation of the rifaximin should not have taken place. It is within ordinary skill to adjust total volumes of solvent and water to rifaximin to provide a second solution wherein the rifaximin is fully dissolved at elevated temperatures, but is concentrated enough that crystallization begins to occur upon cooling to the temperature of 35-40° C. Thus, the next steps of the inventive process are:

(c) cooling the second solution to a temperature of 35-40° C., and stirring at the temperature of 35-40° C. until crystallization takes place, then (d) cooling the solution to about 0° C. with stirring, until crystallized material is present.

As the mixed aqueous organic solvent and dissolved rifaximin are cooled, with stirring, to the temperature of 35-40° C., crystallization begins to take place. Seeding is not necessary. The selection of an appropriate concentration of the rifaximin in the mixed solvent can be determined by routine experimentation, such that the solution is sufficiently concentrated that no rifaximin has precipitated at the reflux temperature, but crystallization begins to occur at the 35-40° C. temperature. The heating of the flask or reactor in which this process is carried out is regulated by means well known in the art, e.g., thermostated oil bath, electrical heating units, and the like. While the first step of the process at reflux does not need close regulation of the thermal input, as the temperature of the solution is self-regulated by the reflux process, the step of cooling from reflux to the 35-40° C. temperature requires accurate thermal regulation, as with a thermostat. Stirring can be carried out by any of the means well-known in the art, such as with the paddle-type overhead stirrer described above. Stirring continues as the reaction is cooled and held at the 35-40° C. temperature. When crystallization is observed to have initiated, e.g., by visual inspection or optical device, heating is discontinued, but stirring is continued, and the solution is cooled to about 0° C., and is continued as the composition containing the crystallizing rifaximin is chilled.

When crystallization has progressed to a satisfactory degree, and is believed to be sufficiently complete for the effective recovery of the rifaximin active ingredient, a valuable material, the crystallized material is recovered by any means known in the art, e.g., filtration, centrifugation, or the like. Thus, the process involves:

(e) recovering the crystallized material, then (f) drying the crystallized material to a water content of between 2.5% and 5.0%;

to provide the composition comprising mixed crystalline polymorphs rifaximin α and rifaximin β.

Once the crystallized material has been recovered, it is dried to a known level of water content, of between 2.5% and 5.0%. Water content of the solid can be determined by methods known in the art, such as Karl Fischer titration. It is also possible to obtain X-ray powder diffractograms of the material, which serves to indicate the relative contents of the rifaximin α and rifaximin β polymorphs in the final product. Other rifaximin polymorphs can also be present, but the predominant polymorphs are the rifaximin α and rifaximin β polymorphs. It is possible that a certain amount of the relatively amorphous rifaximin γ can also be present. As discussed above, a content of about a minority percentage of rifaximin β, or a content of up to 45%, up to 30%, up to 20%, about 3-12% or about 5-8% rifaximin β, with a remaining percentage of refaximin α can be present in the composition comprising mixed crystalline polymorphs rifaximin α and rifaximin β, obtained by practice of a method of the present invention. The majority remainder of the composition can be rifaximin α. The relative proportions can be determined from the X-ray powder diffractograms; the characteristic 2θ diffraction angles are provided in the patent documents cited above, which are incorporated by reference herein in their entireties. In particular, an XRPD pattern showing 2θ absorptions as a doublet at 7.4° and 7.9° as indicative of the α polymorph and 2θ absorptions as a singlet at 5.4° and a triplet at 10.5°, 11.1° and 11.8° as indicative of the β polymorph will indicate the mixed crystals of α and β polymorphs. The full XRPD pattern of the mixed polymorph will also present overlapping and unique 2θ absorptions of the combined XRPD patterns of these two polymorphs.

Drying can be carried out by any of the methods well-known in the art, e.g., under vacuum or in a dry atmosphere, over an absorbent such as anhydrous sodium or magnesium sulfate, and the like. Warming is not necessary, and excessive warming is to be avoided.

When the water content of the solid reaches the level of between 2.5% and 5.0%, inspection of the X-ray powder diffractogram of the sample can reveal that a mixture of rifaximin α and rifaximin β has been obtained, possible comprising additional crystalline polymorphs. This mixture of polymorphs can be suitable for use in administration to a patient or in formulation of a medicament suitable for oral administration. It is within routine skill to evaluate the dissolution parameters of a sample having a defined composition prepared by an embodiment of a method of the invention.

Selection of the organic solvent, the ratio of organic solvent to water, the temperature and time of initial cooling and commencement of crystallization, and the temperature and time of final cooling and collection of the crystallized material can all be determined by the person of ordinary skill using the disclosed subject matter herein in conjunction with ordinary knowledge and routine optimization. The use of different organic solvents can result in changes in optimal solvent to water ratios, temperatures, and concentrations of rifaximin in the liquid milieu. Determination of recoveries of the composition comprising the mixture of rifaximin α and rifaximin β using various conditions can inform the selection of the optimized parameters by the ordinary practitioner.

Similarly, it is within ordinary skill, monitoring the drying process and the ratio of the rifaximin α and rifaximin β in the product by process as disclosed and claimed herein, to obtain a composition suitable for a particular formulation for the rifaximin medicament.

EXAMPLES

Example 1

Preparation of Rifaximin Residue

Example 1A

A sample of 75.4 Grams (0.1 moles) of rifamycin O and 32.4 g (0.3 moles) of 2-amino-4-methyl-pyridine is dissolved in 400 ml of methylene chloride and the obtained solution kept at room temperature for 48 hours. After washing the reaction mixture first with 600 ml of an aqueous 1N solution of hydrochloric acid and then with water, and drying the organic phase over sodium sulfate, the methylene chloride was eliminated by evaporation under vacuum that forms a residue of rifaximin.

Example 1B

A solution of 34.7 g (0.046 moles) of rifamycin O, 14.9 g (0.138 moles) of 2-amino-4-methyl-pyridine and 2.8 g (0.011 moles) of iodine in 200 ml of methylene chloride is kept at room temperature for 24 hours. After adding 20 ml of an aqueous 20% solution of ascorbic acid and stirring for 30 minutes, the reaction mixture is first washed with 400 ml of an aqueous 1N solution of hydrochloric acid and then with water to neutrality. The organic phase is recovered, dried over sodium sulfate and the solvent is evaporated under vacuum.

Example 1C

A sample of 34.7 Grams (0.046 moles) of rifamycin O, 14.9 g (0.138 moles) of 2-amino-4-methyl-pyridine and 2.8 g (0.011 moles) of iodine is dissolved in 150 ml of a 7/3 (v/v) mixture of ethanol/water. The resulting solution is stirred for 18 hours at room temperature, then 2.8 g of iodine added and stirring continued for further 2 hours. The reaction mixture is mixed with 5.3 g (0.03 moles) of ascorbic acid and left to stand for 2 days at a temperature of about 5° C.

Example 1D

As ample of 200 Grams (0.265 moles) of rifamycin O and 65.5 g (0.607 moles) of 2-amino-4-methyl-pyridine is dissolved in 1000 ml of methylene chloride and is kept at room temperature for 40 hours. The reaction mixture is washed with 900 ml of an aqueous 1N solution of hydrochloric acid and then with water to neutrality. The washing liquors are cast off, the organic layer dried over sodium sulfate and the product obtained after evaporating the solvent under vacuum.

Example 1E

A sample of 200 Grams (0.265 moles) of rifamycin O and 65.5 g (0.607 moles) of 2-amino-4-methyl-pyridine is dissolved in 1000 ml of methylene chloride and kept at room temperature for 20 hours in presence of 11 g (0.043 moles) of iodine. Treatment with 130 ml of aqueous 20% solution of ascorbic acid yields the final residue.

Example 1F

A sample of 100 Grams (0.132 moles) of rifamycin O and 57.1 g (0.528 moles) of 2-amino-4-methyl-pyridine is stirred in 400 ml of a 1:1 (v/v) mixture of ethanol/water at room temperature for 20 hours. The obtained solid is washed with a 1:1 (v/v) mixture of ethanol/water and then dried under vacuum.

Example 1G

A sample of 60 Grams (0.08 moles) of rifamycin O and 32.4 g of 2-amino-4-methyl-pyridine is stirred in 120 ml of a 9:1 (v/v) mixture of propylene glycol/ethanol for 18 hours at room temperature and the obtained mixture is left standing for 72 hours. After diluting with 160 ml of a 1:1 (v/v) mixture of 2N aqueous hydrochloric acid/ethanol the reaction mixture is filtered, and the residue collected.

Example 1H

A sample of 100 Grams (0.13 moles) of rifamycin O and 43.3 g (0.39 moles) of 2-amino-4-methyl-pyridine is stirred in 300 ml of a 3:2 (v:v) mixture of isopropanol/water for 16 hours at room temperature. The reaction mixture is subsequently filtered, the solid is washed with the same mixture of solvents used in the reaction and dried under vacuum.

Example 1I

A sample of 100 Grams (0.13 moles) of rifamycin O and 43.3 g (0.39 moles) of 2-amino-4-methyl-pyridine is stirred in 300 ml of a 3:2 (v:v) mixture of tert.-butanol/water for 16 hours at room temperature. The reaction mixture is subsequently filtered, and the solid washed with the same mixture of solvents used in the reaction and dried under vacuum.

Example 2

Crystallization of Rifaximin According to Methods of the Invention

Example 2A

Rifaximin residue obtained, e.g., by any of the above methods, is taken into 80 mL of Ethanol solution and transfer into a 3 necked RB flask stir for 10 mins. The temperature is increased to 70° C. to the reflux temperature of ethanol, and the solution stirred for complete dissolution. Then 30 mL of water are added over a time period of 30 minutes. The solution is then cooled to 35-40° C., then stir for 30 minutes, and observed for crystallization. Once crystallization has begun, the solution is furthered cool to 0° C. and stirred for 4 hrs until complete crystallization has taken place.

Example 2B

Employing the same molar ratio of the solvents as in Example 2A, the residue is taken into methanol solution under the same reaction conditions to obtain the desired product.

Example 2C

Employing the same molar ratio of the solvents as in Example 2A, the residue is taken into n-propanol solution under the same reaction conditions to obtain the desired product.

Example 2D

Rifaximin residue is mixed into 80 mL of acetone and transferred into a 3 necked RB flask, stirring for 10 mins. The temperature is raised to reflux and the solution stirred until complete dissolution occurs. Then 30 mL of water is added over a time period of 30 minutes. The solution is cooled to 35-40° C., and stirred for 30 minutes, observing crystallization. After crystallization has begun, the solution is further cooled to 0° C., stirring for 4 hrs until complete crystallization has occurred. Then the product is filtered and washed with 100 mL water.

Example 3

Drying of Rifaximin to Provide the Composition Comprising Mixed Crystalline Polymorphs Rifaximin α and Rifaximin β

A crystallized sample, recovered from the aqueous organic mixed crystallization solvent, e.g., as outlined in any of Examples 2A-2D, is placed in a suitable container, tray, or the like, and placed under condition for drying, i.e., evaporative removal of the organic solvent, and of the water down to the specified content of between 2.5% and 5.0% by weight, as determined, e.g., by Karl Fischer titration, proton NMR, or other methods well known in the art. Drying can be assisted by partial or complete vacuum, by a stream of dry gas (e.g., nitrogen), and aided by the presence of a water absorbent such as anhydrous sodium or magnesium sulfate. The proportion of the rifaximin β and the rifaximin α in the composition comprising mixed crystalline polymorphs rifaximin α and rifaximin β is readily determined by X-ray powder diffraction, as is well-known in the art and is described in the patent documents cited and incorporated by reference herein.

Formulations

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof.

Compositions containing a compound of the invention can be prepared by conventional techniques, e.g. as described in Remington: *The Science and Practice of Pharmacy*, 19th Ed., 1995, or later versions thereof, incorporated by reference herein. The compositions can appear in conventional forms, for example capsules, tablets, solutions, or suspensions.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any oral route which effectively transports the active compound of the invention to the appropriate or desired site of action.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tableting techniques can contain:

Core:
Active compound (as free compound or salt thereof) 250 mg
Colloidal silicon dioxide (Aerosil®) 1.5 mg
Cellulose, microcryst. (Avicel®) 70 mg
Modified cellulose gum (Ac-Di-Sol®) 7.5 mg
Magnesium stearate Ad.
Coating:
HPMC approx. 9 mg
*Mywacett 9-40 T approx. 0.9 mg
*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for the manufacture of a composition comprising mixed crystalline polymorphs rifaximin α and rifaximin β, comprising:

(a) dissolving rifaximin in a water-soluble organic solvent and warming the organic solvent to reflux; then, when the rifaximin is completely dissolved in the organic solvent to provide a solution of rifaximin in the organic solvent, (b) adding water to the solution to provide a second solution of rifaximin in a mixed solvent, the mixed solvent having an organic solvent to water ratio of about 5:5 to about 9:1 (v/v), to provide the second solution of rifaximin in the mixed solvent; then, (c) cooling the second solution to a temperature of 25-50° C., and stirring at the temperature of 25-50° C. until crystallization takes place, then (d) cooling the solution to about 0° C. with stirring, then, (e) recovering the crystallized material, then
(f) drying the crystallized material to a water content of between 2.5% and 5.0%;
to provide the composition comprising mixed crystalline polymorphs rifaximin α and rifaximin β, wherein the composition comprising mixed crystalline polymorphs rifaximin α and rifaximin β contains about 3% up to about 12% (w/w) of the rifaximin β crystalline polymorph in mixture with a remaining percentage of the rifaximin α crystalline polymorph.

2. The method of claim 1, wherein the organic solvent to water ratio is about 7:3 (v/v).

3. The method of claim 1, wherein cooling the second solution is to a temperature of 35-40° C., and stirring at the temperature of 35-40° C. continues until crystallization takes place.

4. The method of claim 1, wherein the water-soluble organic solvent is an alcohol.

5. The method of claim 4, wherein the alcohol is ethanol.

6. The method of claim 4, wherein the alcohol is methanol, isopropanol, or n-propanol, or any mixture thereof.

7. The method of claim 1, wherein the water-soluble organic solvent is a ketone.

8. The method of claim 7, wherein the ketone is acetone.

9. The method of claim 1, wherein the water-soluble organic solvent is a mixture of an alcohol and a ketone.

10. A rifaximin composition comprising mixed crystalline polymorphs rifaximin α and rifaximin β prepared by the method of claim 1, containing about 3-13% (w/w) of the rifaximin β crystalline polymorph in mixture with a remaining percentage of the rifaximin α crystalline polymorph.

11. A method of treatment of a condition in a patient for which rifaximin is medically indicated, wherein the condition comprises a gastrointestinal (GI) infection and the composition is administered orally, comprising administration to the patient of an effective amount of a rifaximin composition prepared by the method of claim 1 or of a rifaximin composition of claim 10.

12. A pharmaceutical composition for oral administration comprising an effective amount of a rifaximin composition prepared by the method of claim 1, or of a rifaximin composition of claim 10.

* * * * *